United States Patent [19]
Dvoretzky et al.

[11] Patent Number: 5,534,021
[45] Date of Patent: Jul. 9, 1996

[54] HEATING PAD FOR PROVIDING HEAT THERAPY

[76] Inventors: Israel Dvoretzky, 39 Gateway, Hamden, Conn. 06514; John E. Kuleza, 235 Wethersfield Rd., Berlin, Conn. 06037

[21] Appl. No.: 299,449

[22] Filed: Sep. 1, 1994

[51] Int. Cl.⁶ .................................................. A61F 7/00
[52] U.S. Cl. ............................ 607/112; 607/114; 126/204; 165/46
[58] Field of Search ........................... 607/108–112, 114; 126/204; 165/46

[56] References Cited

U.S. PATENT DOCUMENTS

| | | |
|---|---|---|
| 4,078,552 | 3/1978 | Chen et al. . |
| 4,190,054 | 2/1980 | Brennan ................................ 607/112 |
| 4,735,203 | 4/1988 | Ryder et al. . |
| 4,886,063 | 12/1989 | Crews ................................... 607/114 |
| 5,000,176 | 3/1991 | Daniel ................................... 607/108 |
| 5,027,801 | 7/1991 | Grim ..................................... 607/111 |
| 5,342,412 | 8/1994 | Ueki ...................................... 607/114 |

FOREIGN PATENT DOCUMENTS 8402071  6/1984  WIPO ..................................... 607/108

OTHER PUBLICATIONS

Surgicutt Brochure (Undated).

*Primary Examiner*—Lee S. Cohen
*Assistant Examiner*—Robert Nasser
*Attorney, Agent, or Firm*—Melvin I. Stoltz

[57] ABSTRACT

By providing a carrier constructed for securely retaining a heat generating pad while also being able to be easily, securely mounted to the skin surface of an individual, a delivery system is achieved for providing heat therapy to any desired site or location. The heat generating pad is securely retained using either permanent or separatable fastening means. By employing separatable fastening means, the same carrier can be repeatedly employed by changing to a new heat generating pad after the previously used pad is exhausted. In addition, the carrier incorporates either adhesive means for mounting the carrier and pad to a user or employs separatable fastening means mounted to the carrier to enable the carrier and pad to be easily positioned, wherever desired, and securely retained in that position by engaging the fastening means.

18 Claims, 2 Drawing Sheets

HEATING PAD FOR PROVIDING HEAT THERAPY

TECHNICAL FIELD

This invention relates to a treatment system for providing heat and more particularly to a delivery system employing a pre-packaged, easy to use support assembly for providing a continuous source of heat to the surface of the skin for enabling medicinal heat benefits to be realized.

BACKGROUND ART

It has been found that many medical problems which affect individuals can be successfully treated by applying heat to the affected area. Although a variety of devices have been created for use by individuals to provide heat to a particular area of the body, no system has been achieved which is capable of providing reliable, controlled, repeatable delivery of a precise temperature level in an easily used and convenient form.

The use of heat therapy for many transitory problems, such as pains, muscle pulls, etc., has been practiced for many years. Typically, these maladies are treated with electrically heated pads, hot towels, and/or hot compresses.

In addition to these common maladies, other medical problems have been found to benefit from the direct application of heat to a particular location on the body. A prime example of such medical problems which has recently been found to be treatable with heat therapy is warts.

Warts are very common and have long presented problems to individuals due to the pain, discomfort and the cosmetic problems associated therewith. Although various methods and treatments have been developed over the years for reducing or eliminating the undesirable effects associated with warts, these prior art applications, treatments and methods have been incapable of eliminating or curing warts or the problems associated with them.

In order to understand the treatment of warts, it is important to know that the skin is divided into three layers, the epidermis, the dermis, and the subcutaneous tissue. The outer layer of the skin is called the epidermis, and varies in thickness from about 0.3 mm on the eyelids and flexural areas to 1.55 mm on the palms and soles. The outermost layer of the epidermis is the stratum corneum (horny layer), which is comprised of completely keratinized dead cells. The thickness of the stratum corneum varies greatly on different parts of the body, being thickest on the palms and soles and totally absent on the oral mucosa.

The bottommost layer of the epidermis, called the basal cell layer, rests upon the basement membrane separating the epidermis from the dermis. The basel cells are the only epidermal cells that proliferate. The basal cells proliferate and, by cell division, form the keratinocytes (squamous cell layer, stratum spinosum, spinous layer). The keratinocytes synthesize insoluble protein which remains in the cells and will eventually become a major component of the outer layer (the stratum corneum, horny layer). The keratinocytes continue to divide and to migrate from the bottommost layer to the outermost layer, until the cells finally die. In this process of keratinization, the cells continue to flatten and their cytoplasm appears granular (stratum granulosum, granular layer) until they finally die as they reach the surface to form the stratum corneum (horny layer).

Warts are known to be intra-epidermal tumors of the skin caused by infection with the human papilloma virus (HPV). The HPV induces an abnormal increase of cells in the skin tissue, commonly referred to as hyperplasia, with the hyperplasia being limited to the squamous epithelium. Typically, replication of the papilloma virus is confined to the nuclei of the upper layer of infected epidermal cells.

Many different methods and application systems have been developed to treat warts. However, none of them are uniformly effective. The most common treatments for eliminating warts are surgery (conventional or laser surgery), cryosurgery, or the application of different acidic or caustic chemicals in order to completely remove the affected area. However, for many individuals, these processes are as difficult or as uncomfortable as the wart condition itself. The warts may return, and patients may be left with pain and/or scar formation. Consequently, many individuals avoid these treatments and, instead, merely accept the discomfort associated with their warts. Unfortunately, when warts are left alone, they may also spread, as a viral-infectious process.

Various chemical compositions have been developed in an attempt to eliminate or reduce the size of the warts by inactivating or slowing the growth of the virus within the skin. In addition, other chemical compounds have been used to reduce or eliminate the overgrowth and keratinization of the wart and thereby lessen its sensitivity or tenderness. Unfortunately, these chemical compositions have been incapable of providing a universally successful treatment for warts and, at best, have only been partially successful.

It has long been known that temperature is an important factor in the development of warts, as well as in treating warts. It is also known that the vast majority of warts are produced by HPV types 1, 2, 3, and 4. These viruses prefer to produce lesions on the acral (end) parts of the body which are cooler than the rest of the body. Since the skin surface in general and the extremities of individuals, such as hands and feet, typically have temperatures of between about 24° and 31° C., (less than the body temperature) these locations are typical for the development of the wart virus. The anogenital warts and laryngeal warts tend to replicate in more warmer locations and are clearly well known as comprising a different HPV.

Various studies have shown that the local application of heat causes the virus organisms to be slowed or inactivated. One attempt to effectively apply heat as a wart treatment was the use of hot water baths, with the individual immersing the entire body part containing the wart into a hot water bath. In view of the inherent limitations of this system as well as its limited success, wide acceptance of hot water exposure was never realized.

In particular, one principal limitation found with hot water baths is the inherent difficulty in maintaining a constant temperature for long time periods. In addition, hot water baths are extremely difficult to employ since the entire body part, not only the wart, must be immersed into the hot water. This is particularly difficult since long time exposures are required, as well as repeated exposures several times a day. Furthermore, the hot water bath procedure is particularly hazardous to children due to the risk of severe burning.

Finally, hot water baths are not realistically practical due to the importance of precision in the application temperature. The application temperature is extremely important, since the leeway between a therapeutic temperature and a destructive temperature is very narrow. At 44° C., a six-hour exposure is needed to cause blistering or irreversible damage to the basal layer of the epidermis. However, at 51° C., an exposure of between about 3 to 5 minutes is sufficient to destroy the epidermis.

As is evident from this discussion, warts can be effectively treated if a dependable delivery system for providing heat therapy were available. Similarly, numerous other medical problems are also effectively treated using a similar dependable delivery system which provides controlled heat therapy.

Therefore, it is a principal object of the present invention to provide a delivery system for providing heat therapy which is easy to use and is highly effective in providing controlled temperature levels to any desired location on the skin or body of the user.

Another object of the present invention is to provide a delivery system for providing heat therapy having the characteristic features described above which is capable of providing a constant level of heat for extended periods of time.

Another object of the present invention is to provide a delivery system for providing heat therapy having the characteristic features described above which is easily used by a consumer and enables the heat delivery system to be retained in any desired position or location for any desired length of time.

A further object of the present invention is to provide a delivery system for providing heat therapy having the characteristic features described above which is capable of being constructed to be easily reused with removable and replaceable heating pads cooperatively associated therewith, whenever required.

Another object of the present invention is to provide a delivery system for providing heat therapy having the characteristic features described above which is capable of being constructed as a single-use system which is easily applied to the skin surface for attaining the desired heat benefits and then disposed after use.

Another object of the present invention is to provide a delivery system for providing heat therapy having the characteristic features described above which is capable of providing consistent, repeatable, reproducible, and reliable temperature levels in a convenient, easily attained manner.

Other and more specific objects will in part be obvious and will in appear hereinafter.

SUMMARY OF THE INVENTION

In the present invention, the difficulties and drawbacks of the prior art systems, methods, and procedures have been eliminated and a local, easily employed, convenient consumer-oriented heat therapy treatment system is achieved. In this invention, a delivery system is provided which comprises a support system incorporating an exothermic pad. Using the present invention, the delivery system is easily applied directly on the skin surface, providing heat to the precisely desired area, so as to attain the benefit of the heat therapy at the site of the particular medical problem. No prior art delivery system of this nature has ever been taught or suggested.

Exothermic pads have been previously developed and typically comprise a porous film or pad of woven or non-woven material incorporating chemicals which will react exothermically to generate heat in the presence of oxygen. Although any desired chemicals can be employed, exothermic pads typically contain moxa or a mixture of iron powder, activated charcoal, wood fibers, water, and salt. Alternatively, a mixture of alkaline sulfides and iron carbide are employed with the chemicals stored in an inert, oxygen-free, chamber and exposed to oxygen prior to use. In addition, the pores of the pads are of sufficient size to assure the required air flow is achieved.

Prior to use, the pad is typically sealed within a pouch using an inert gas, such as nitrogen. As long as the pad remains in the sealed container until use, no chemical reaction takes place. However, once the pad is opened, the presence of the oxygen in the air causes the chemicals to react and the desired exothermic reaction is produced.

In the present invention, the delivery system incorporates an exothermic pad which is one component in a carrier system which enables the user to easily and conveniently apply the pad to any desired location and maintain the pad in the desired position. Once in position, the pad is applied to the skin at the site of the malady being treated and allowed to remain on the skin for several hours. This procedure may be repeated as necessary.

By applying the exothermic pad in this manner in treating warts, the wart virus is inactivated or slowed in its development, thereby preventing further invasion of the virus to adjacent tissue. As a result, the normal reparative process of the skin takes effect, moving the infected portion to a higher and higher level in the spinous layer of the epidermis, towards the surface of the skin, until the wart is shed in the normal process with the stratum corneum.

Although the treatment of warts is only one example of the medical problems that can be effectively treated using the heat therapy delivery system of this invention, the use of the present invention for treating warts is fully detailed herein. However, it is to be understood that the efficacious use of the present invention for treating warts is described herein for exemplary purposes only, and no limitation of the present invention to warts is intended. Furthermore, particular temperature levels and exposure times detailed herein are provided as examples of the present invention, and other temperatures or exposure times for other medical treatments can be attained with the present invention and are encompassed within the scope of the present invention.

By employing the delivery system of the present invention, the temperature of the skin is elevated and maintained at about 42°–43° C. for a period of about two hours or more using an exothermic pad. Preferably, however, the delivery system should remain on the skin for about six to seven hours and then replaced with a new pad. This treatment should continue for several days or weeks, as long as the skin surface shows no signs of being adversely affected.

It has been found that the skin can tolerate definite amounts of local hyperthermia without blistering or being damaged. Furthermore, it has also been found that the skin surface can tolerate an external temperature of 44° C. without blistering and, even at that temperature, will take at least six hours of continuous exposure before blistering will occur. In addition, even if slight blistering were to occur, such blistering may well enhance the recovery of warts, since it would eliminate some of the upper layer of the wart.

If desired, several layers of sterilized gauze, or similar material, can be placed between the skin surface and the pad to reduce the heat exposure to the skin. One method available to treat warts today is using cryosurgery with liquid nitrogen. In this method, there is blister formation which is supposed to help in the elimination of the wart.

If desired, keratolytic chemical agents may be incorporated with and/or into the exothermic pad to assist in reducing the thickness of the epidermis, particularly the stratum corneum. Inasmuch as the wart viruses are confined to the upper layer of the epidermis, the stratum granulosum and stratum corneum, any removal of the outermost horny layer technically eliminates a portion of the wart as well as the viral particles contained therein, destroying the viral particles by shedding. In addition, the thinning of the stratum corneum enables the heat to penetrate deeper within the wart lesion, thereby achieving greater efficacy from the application of the pad.

Although various keratolytic agents can be incorporated with and/or into the exothermic pad in order to reduce the upper layer of the epidermis, it has been found that salicylic acid or salicylic and lactic acid are preferable, since such chemicals may be incorporated with and/or into the exothermic pad to attain the desired beneficial results. By incorporating either salicylic acid, salicylic and lactic acid, or other similar chemical compositions, the exothermic pad may operate more effectively, since the thickness of the epidermis is reduced, thereby allowing the heat generated by the exothermic pad to penetrate the wart to a greater extent.

In order to further enhance the efficacy of the present invention, it is preferable to remove the layers of dead skin that have resulted from the application of the keratolytic chemical agents. Consequently, after each use of the delivery system of this invention, it is desirable for the user to gently rub the affected area with an abrasive member, in order to reduce the thickness of the epidermis, particularly the stratum corneum. Typically, any mildly abrasive member may be employed, such as an emery board, manicure nail file, wash cloth, brush, etc. In this way, the process of reducing the thickness of the epidermis is enhanced and the removal of the wart, as well as the inactivation of the wart virus is accomplished more rapidly.

Although the delivery system is capable of being constructed in a plurality of alternate embodiments, each of these embodiments comprise two principal constructions. In one construction, the delivery system is reusable, while in the other construction, the delivery system is employed for a single use or application.

In the constructions designed for reusability, the delivery system of the present invention comprises a support assembly which enables heating pads to be removably secured thereto. In this way, the same support assembly is repeatedly used, with new heating pads being secured affixed thereto whenever needed. As a result, the ability of each heating pad to provide a desired level of heat for a finite period of time is easily accommodated, with a new heating pad being quickly and easily mounted to the support assembly whenever extended exposure time of elevated temperatures are required.

In the alternate principal construction, the delivery system is specifically designed for a single use and is generally constructed with the heating pad securely affixed to the carrier or support assembly. In some instances, a single use delivery system is preferred or is able to be applied to areas of the body where a reusable system is not easily affixed.

Regardless of whether a single use delivery system or a reusable delivery system is employed, both constructions are capable of having the life of the heating pad extended, if only short-term application is required. As detailed above, typical heating pads are generally controlled by the presence of oxygen which causes the exothermic reaction to occur.

Consequently, by sealing the heating pad and, if desired, the entire delivery system in a sealed container, the necessary oxygen supply is eliminated and the chemical reaction can be stopped. Thereafter, whenever reapplication of the heating pad to the desired surface is sought, the delivery system is removed from the sealed container and reapplied to the desired site. In this way, greater use and enhanced flexibility and benefits are realized by the consumer.

The invention accordingly comprises an article of manufacture possessing the features, properties, and relation of elements which will be exemplified in the article hereinafter described and the scope of the invention will be indicated in the claims.

THE DRAWINGS

For a fuller understanding of the nature and objects of the invention, reference should be had to the following detailed description taken in connection with the accompanying drawings, in which:

FIG. 6 is a top plan view of a still further alternate embodiment of a single use delivery system of the present invention.

DETAILED DESCRIPTION

By referring to FIGS. 1–5, along with the following detailed disclosure, the construction and use of alternate embodiments of the universally applicable delivery system of the present invention can best be understood. As detailed herein, the delivery system of the present invention is manufacturable as both a reusable system and a single use system. Furthermore, as is evident from this disclosure, the present invention can be attained in other variations, not shown in this disclosure. Consequently, it is to be understood that the embodiments depicted in FIGS. 1–5 and discussed herein are presented for exemplary purposes only and are not intended to limit the scope of the present invention.

In addition, as discussed above, the heat therapy delivery system is employable for a wide variety of purposes and application needs. As an example of the uses for the present invention, the treatment of warts has been selected and employed herein. However, although the use of the present invention for treating warts is detailed herein, this discussion is for exemplary purposes only, and the scope of the present invention is not intended to be limited thereto.

Figure 1:
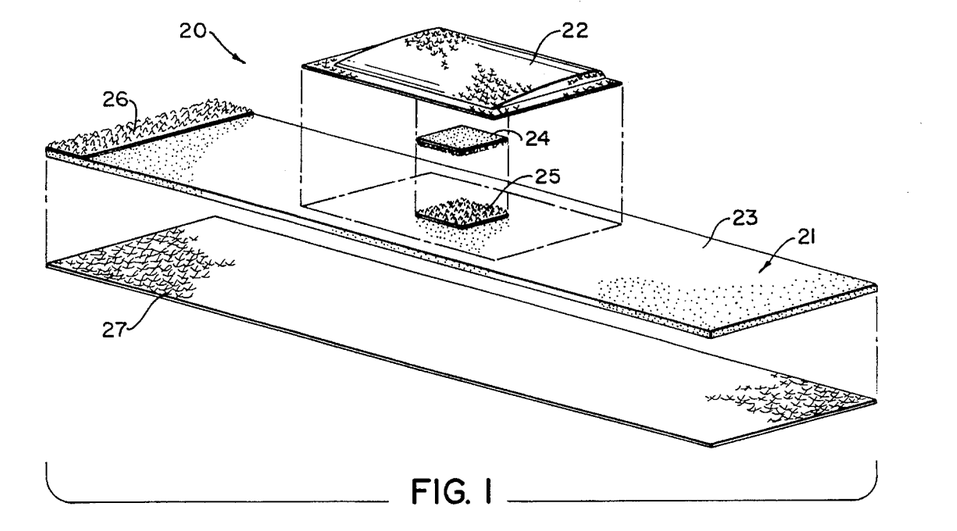
FIG. 1 is an exploded perspective view of a reusable delivery system constructed in accordance With the present invention.

In FIG. 1, one embodiment of the delivery system 20 of the present invention is fully depicted. In this embodiment, delivery system 20 is constructed to be repeatedly reused and incorporates an elongated, substantially continuous carrier 21 to which heating pad 22 is removably mounted. Preferably, carrier 21 is formed in this embodiment, from a single sheet of porous material 23.

In this embodiment, heating pad 22 is removably mountable to carrier 21 by employing fastening means, depicted as hook and loop fasteners portions 24 and 25. In this embodiment, hook/loop fastener portion 25 is securely affixed to a surface of carrier 21, while hook/loop fastener 24 portion is securely affixed to heating pad 22. As a result, whenever a new heating pad 22 is needed, heating pad 22, with hook/loop fastener portion 24 affixed thereto, is mounted to hook/loop fastener portion 25 of carrier 21, thereby securely affixing heating pad 22 in the precisely desired position on carrier 21.

In the preferred construction, hook/loop fastener portion 24 is preferably constructed with an adhesive coating or layer affixed to the rear surface thereof to enable fastener portion 24 to be securely mounted to any heating pad 22, when desired. Similarly, hook/loop fastener portion 25 can be secured to carrier 21 in the same manner or, alternatively, can be permanently mounted to carrier 21 during the manufacture of carrier 21.

The construction of this embodiment of delivery system 20 is completed by securing additional fastening means to carrier 21 which will enable carrier 21 to be easily and conveniently securely affixed to any desired location on the user's body in a manner which will allow heating pad 22 to overlie the wart, or otherwise affected area, enabling the treatment provided by delivery system 20 to be effectively employed. While various fastening means can be used, in accordance with the scope of the present invention, FIG. 1 depicts the use of a conventional hook and loop fastening system which incorporates fastening portions 26 and 27.

As depicted in FIG. 1, in this embodiment, fastener portion 26 is mounted along an edge of carrier 21, preferably on the same surface to which fastener portion 25 is mounted. In addition, fastener portion 27 comprises an elongated, substantially continuous sheet, has a size and shape substantially identical to the size and shape of carrier 21, and is securely affixed to carrier 21 on the opposed surface of fastener portion 26. By employing this construction, fully assembled delivery system 20 is quickly and easily securely mounted to virtually any desired location on the body of the user.

In order to employ delivery system 20, heating pad 22 is mounted to carrier 21 and, once securely affixed in the desired position, heating pad 22 is placed in contact with the body area to be treated. Then, carrier 21 is wrapped around that portion of the body, the end of carrier 21 bearing fastener portion 26 being wrapped around the body portion as the final step. Securement of delivery system 20 is attained by bringing the surface of fastener portion 26 into contact with the exposed surface of fastener portion 27, enabling the hook and loop fastening members thereof to lockingly interengage.

By employing delivery system 20 as detailed above, system 20 is quickly, easily, conveniently, and securely affixed to the body of the user with heating pad 22 overlying the wart to be treated, delivering the desired heat directly to the affected zone. As is apparent to one of ordinary skill in this art, delivery system 20 can be constructed in any desired width or length or in any desired configuration in order to enable delivery system 21 to be capable of being securely mounted to virtually any desired location where wart treatment or heat therapy is desired.

Although various alternate shapes and construction arrangements are detailed herein, further alternate variations may be employed without departing from the scope of the present invention. Furthermore, hook/loop fastening means as detailed above and shown throughout the drawings, are merely exemplary of the various fastening systems that can be employed without departing from the scope of this invention.

As discussed in detail above, exothermic heating pads 22 are well known in the art and have been available in various alternate sizes as well as alternate constructions. As stated above, exothermic pads typically comprise a porous film or pad of woven or non-woven material incorporating chemicals therein which will react exothermically in the presence of oxygen. In alternate constructions, different chemicals are maintained in separate chambers and, upon use, the chambers are ruptured and the chemicals intermixed to produce the exothermic reaction. In the present invention, any desired exothermic pad can be employed in achieving the delivery system of the present invention.

Although exothermic pads are well known and have been widely used for various purposes prior to the present invention, an easily employed, pad holding and securely affixing delivery system has never been achieved prior to the present invention. By employing this invention, a substantial advance has been attained and treatment of conditions by heat application can be realized in a convenient, dependable and easily used manner.

In achieving the present invention, various materials can be employed as layer 23 of carrier 21. In general, the material employed for layer 23 of carrier 21 should possess strength and durability for repeated use, light weight, and flexibility for being easily positioned in any desired location on the user's body and the ability to insulate and enable oxygen to flow therethrough. In the preferred construction, layer 23 of carrier 21 is formed from a polyurethane sheet cut to the desired size and shape, with the polyurethane sheet preferably being of a cosmetic and/or medical quality or grade.

Some unique advantages attained by employing the preferred type of material for carrier 21 in achieving delivery system 20 is the ability to deliver oxygen to heating pad 22 while also providing a high degree of insulation for concentrating the heat when desired. In this way, the heat generated by pad 22 is concentrated on the body part, enabling the unique advantages of heat therapy to be optimized.

It has also been found that by controlling the porosity and the thickness of layer 23, the desired oxygen flow and heat insulation properties are precisely controlled. This assures the attainment of a delivery system which is effective and provides the desired results in a consistent and repeatable manner.

In addition to controlling the thickness of layer 23 and the size of the pores incorporated therein, the desired insulation effect and oxygen flow are also controlled by varying the cell structure of layer 23. This is most effectively achieved by controllably varying such physical characteristics as the ratio of open cells to closed cells found in layer 23, or the reticulated or non-reticulated nature of layer 23. By employing these factors and varying these factors, as desired, a precise oxygen flow rate and insulation level can be attained for achieving any desired result.

In the test results conducted using polyurethane as the material for carrier 21, it has been found that the thickness of the polyurethane layer preferably ranges between about one-eighth and one-quarter inches. Although this range is preferred, carrier 21 may comprise a thickness of between about one-sixteenth and one-half inches. In addition, the pore size of the material varies between about 0.05 and 3.0 mm. In the preferred embodiment, the pore size ranges between about 0.1 and 0.5 mm.

Although the construction detailed above for carrier 21 is preferred when employing polyurethane material, these dimensions and porosity values can be widely varied without departing from the scope of the present invention. In addition, any other equivalent material can also be employed in accordance with this invention. In general, any material capable of being formed in a substantially continuous porous sheet configuration can be effectively employed for carrier 21. Such alternate materials include polystyrenes, polyolefins, and polypropylenes. However, this list is not exhaustive and is merely exemplary of the types of material employable as carrier 21 in accordance with this invention.

Figure 2:
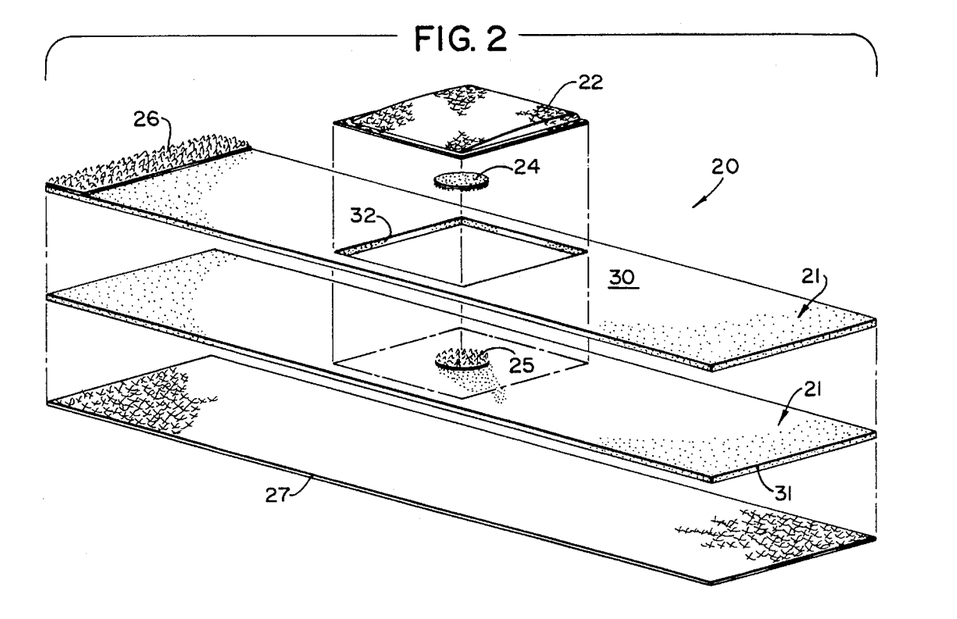
FIG. 2 is an exploded perspective view of an alternate embodiment of a reusable delivery system manufactured in accordance with the present invention.

In FIG. 2 an alternate embodiment of delivery system 20 is depicted. In this embodiment, delivery system 20 comprises a reusable construction similar to the construction detailed above in reference to FIG. 1. However, in the embodiment depicted in FIG. 2, carrier 21 is formed from two, independent, elongated layers 30 and 31 of porous material which are integrally bonded or affixed to each other to form carrier 21.

In this embodiment, heating pad 22 incorporates hook/loop fastener portion 24 mounted thereto, as detailed above, with cooperating hook/loop fastener portion 25 securely affixed to porous material layer 31. In addition, hook/loop fastener portion 27 which comprises an elongated sheet having substantially the same dimensions as porous material layer 31 is integrally bonded, fused, or affixed to the surface of layer 31 which is opposed from the surface to which fastener portion 25 is affixed.

In this embodiment, fastener portion 26 is affixed along one edge of layer 30 of carrier 21, positioned, as detailed above, for cooperative, locking interengagement with fastener portion 27 at any desired location along the length thereof. In addition, in this embodiment, layer 30 incorporates a cutout zone 32 which is dimensioned for peripherally surrounding and substantially enveloping heating pad 22 when heating pad 22 is mounted in engagement with fastener portion 25.

By employing this construction, heating pad 22 is peripherally surrounded and substantially embedded within carrier 21, thereby further enhancing the insulation effect provided by carrier 21 and providing added concentration of the heat generated by pad 22. Furthermore, by incorporating cutout zone 32 in layer 30 of carrier 21, the surface of heating pad 22 to be applied to the wart area is substantially co-extensive with the surface of layer 30. In this way, any unwanted movement or possible dislodgement of heating pad 22 from its locked, interengagement with carrier 21 is substantially eliminated.

In operation, the delivery system 20 depicted in FIG. 2 is mounted to any desired position or location on the body of the user in a manner detailed above in reference to FIG. 1. In general, pad 22 would have fastener portion 24 securely affixed to one surface thereof, with pad 22 and fastener portion 24 then positioned within cutout zone 32 of layer 30 in secure, locking engagement with fastener portion 25 of layer 31.

With heating pad 22 in the precisely desired secure position embedded within carrier 21, pad 22 is placed on the treated body area and delivery system 20 is then securely mounted in the precisely desired position. This is easily achieved by merely placing one end of carrier 21 and integrally attached fastener portion 27 about the portion of the body being treated with the opposed end of carrier 21 and fastener portion 27 which incorporates fastener portion 26 being wrapped about the remaining portion of the user's body in a manner which will bring fastener portion 26 into engagement with the exposed surface of fastener portion 27. Once placed in interengagement with each other, fastener portions 26 and 27 are lockingly engaged, thereby securely mounting delivery system 20 in the precisely desired position, with heating pad 22 overlying the body area, providing the medicinal heat benefits directly to the desired area.

In the preferred construction, each layer 30 and 31 forming carrier 21 is formed from polyurethane material having substantially the same thickness and porosity. Of course, if desired, layers 30 and 31 can be varied both in material as well as in thickness or porosity. In this way, any desired oxygen flow and insulation effect can be easily achieved to enhance the benefits provided by delivery system 20 of this invention.

Although layers 30, 31 and fastener portion 27 can be intimately affixed to each other in any desired manner, intimate bonding or lamination of each of the layers to each other is preferred. By employing bonded lamination, integral affixation of each layer in its entirety is assured and unwanted air gaps which might otherwise affect the performance of delivery system 20 are avoided.

In each of the embodiments detailed above and shown in FIGS. 1 and 2, heating pad 22 is removably mountable to carrier 21. In this way, the resulting delivery system 20 is capable of being easily and conveniently repeatedly reused as required by the consumer.

In this regard, since heating pad 22 is capable of providing the desired heat level for a finite length of time, once heating pad 22 has been fully expended and is incapable of providing the requisite heat, pad 22 is removed from carrier 21 by separating fastener portion 24 from fastener portion 25. Heating pad 22 is then discarded and a new, fresh heating pad is removed from its packaging, activated in the desired manner, with a new hook/loop fastener portion 24 affixed to one surface thereof. Then, the new heating pad 22 is placed in interengagement with fastener portion 25, securing new heating pad 22 to carrier 21 in order to enable delivery system 20 to be applied to the treated area and continue the requisite heat therapy.

This process is repeated as many times as is necessary to attain the desired therapeutic result. By providing delivery system 20 with the construction detailed above, which enables carrier 21 to be repeatedly employed with different heating pads 22 as desired, a cost effective treatment system is realized. In addition, the user is able to enjoy the benefits provided by a delivery system capable of being easily securely positioned in any desired location for delivering optimum heat therapy to selected areas of the body.

Figure 3:
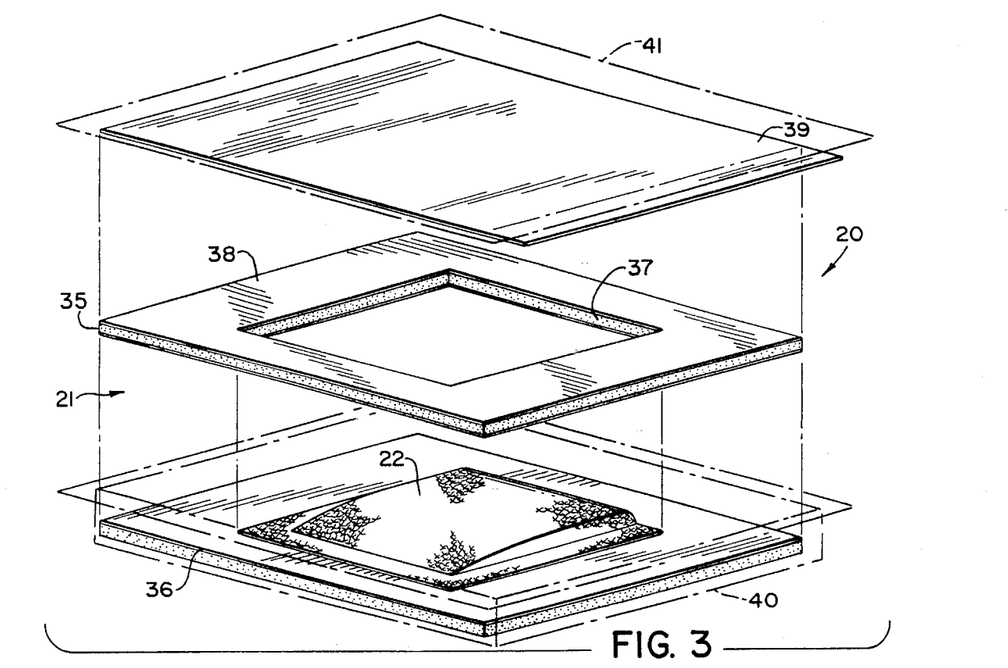
FIG. 3 is an exploded perspective view of one embodiment of a single use delivery system manufactured in accordance with the present invention.
Figure 4:
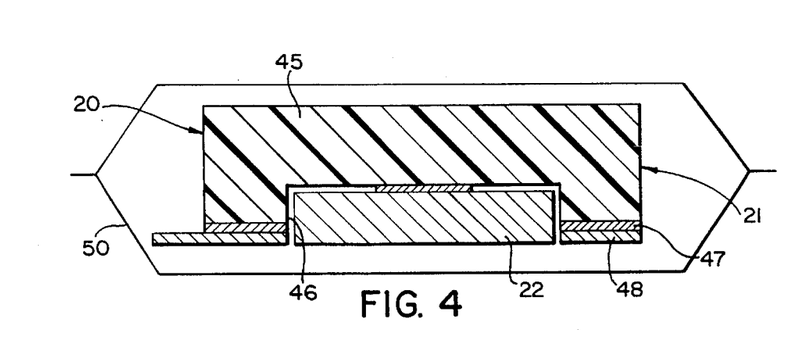
FIG. 4 is a cross-sectional side elevation view of an alternate embodiment of a single use delivery system manufactured in accordance with the present invention, depicted in a sealable container.
Figure 5:
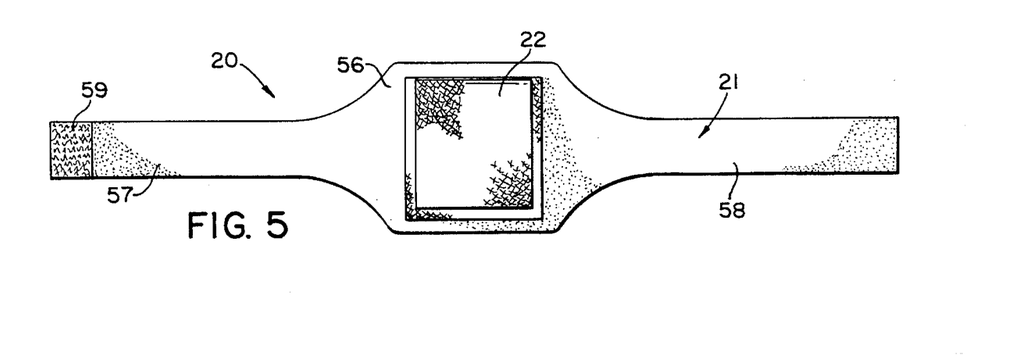

Although a reusable delivery system is most economical and is probably the system employable for most situations, some applications may require a single use delivery system. In FIG. 3–5, examples of alternate constructions for attaining an effective, single-use delivery system 20 are detailed.

In FIG. 3, delivery system 20 incorporates a carrier 21 which is formed from porous material layers 35 and 36. In the preferred embodiment, porous material layers 35 and 36 are both formed from polyurethane material, as detailed above. However, any other equivalent material can be employed without departing from the scope of this invention.

In the preferred construction, heating pad 22 is securely mounted to one surface of layer 36 while layer 35 incorporates cutout zone 37 constructed for peripherally surrounding and enveloping heat pad 22. In this way, heating pad 22 is peripherally surrounded and enclosed by layers 35 and 36 of carrier 21, thereby enhancing the oxygen flow capabilities and insulation capability attained by layers 35 and 36 of carrier 21. Furthermore, since this embodiment is constructed for a single use, heating pad 22 is preferably securely bonded or affixed to the surface of layer 36, since its removability from carrier 21 is not required.

In order to enable delivery system 20 of this embodiment to be easily applied to any desired location and securely affixed thereto, an adhesive coating 38 is applied to the exposed surface of layer 35, preferably covering the exposed surface substantially in its entirety. In addition, in order to protect adhesive coating 38, while enabling delivery system 20 to be securely affixed to any desired location, a release liner 39 is employed to overlie adhesive coating 38 and protect adhesive coating 38 until its application to the desired surface is sought.

This embodiment of delivery system 20 is quickly and easily mounted in overlying, contacting, and peripherally surrounding engagement with virtually any position on the body of the user after release line 39 is removed. In using delivery system 20 of this embodiment, heating pad 22 is activated in the appropriate manner, depending upon the type of heating pad employed.

Preferably, with this embodiment, system 20 employs a heating pad 22 which is activated when exposed to oxygen. Consequently, system 20 is mounted in a sealed container which is packaged with an inert gas, such as nitrogen.

In FIG. 3, a typical sealed container 40 is shown in phantom, with container 40 incorporating an internal retaining zone within which system 20 is securely retained. As depicted, container 40 is sealed by mounting removable cover 41 thereto. By employing container 40 and cover 41, system 20 is retained for any desired length of time with heating pad 22 being inactivated. However, when cover 41 is removed to use system 20, heating pad 22 is activated by its exposure to atmospheric oxygen.

If desired, other activation systems for heating pad 22, such as sealed chemicals in a chamber, may be employed with pad 22 being activated in the appropriate manner. If sealed container 40 is not required, this component can be eliminated.

Then, heating pad 22 is placed on the wart, with adhesive coating 38 contacting the skin of the user. By pressing carrier 21 to the skin surface, complete, secure affixation of adhesive coating 38 to the skin is assured and delivery system 20 is securely affixed in the desired position. Once mounted in position, delivery system 20 remains in overlying cooperative interengagement with the wart, delivering the desired therapeutic heat to the desired location.

In this embodiment, layers 35 and 36 are preferably constructed from polyurethane material, as detailed above. However, if desired, any other equivalent material can be employed which provides the desired oxygen flow and insulation characteristics.

Layers 35 and 36 may be constructed with any desired thickness, cell configuration and porosity which provides the desired physical characteristics being sought. In general, the only preferred construction for layer 35 is the construction of layer 35 with a thickness substantially equivalent to, or slightly less than, the thickness of heating pad 22. In this way, the top surface of heating pad 22 will be substantially co-extensive with, or slightly above, the surface established by adhesive coating 38.

By employing this construction, ease of mounting delivery system 20 of FIG. 3 is realized and a more comfortable construction is attained, with heating pad 22 lying directly on the treated area, while the surface established by adhesive coating 38 is in direct contact with the skin of the user. As a result, unwanted stretching or pulling by delivery system 20 is eliminated and a more comfortable, easily employed and mounted delivery system is realized.

In FIG. 4, an alternate construction for a single use delivery system is depicted. In this embodiment, delivery system 20 is similar to the delivery system shown in FIG. 3 and detailed above. In addition, FIG. 4 also depicts delivery system 20 in a sealed container typical of the type of container that would normally be employed for commercially distributing a single use delivery system which employs an oxygen activated heating pad.

In this embodiment, delivery system 20 comprises a carrier 21 which is formed from a single layer 45 of flexible, porous material possessing the physical characteristics required to attain the desired level of oxygen permeability and insulation. In addition, layer 45 of carrier 21 incorporates a cavity 46 formed therein dimensioned for receiving heating pad 22. In the preferred construction, cavity 46 is dimensioned for receiving heating pad 22 substantially in its entirety, with the surface of layer 45 which peripherally surrounds pad 22 being substantially coextensive with the exposed surface of pad 22.

In addition, an adhesive coating 47 is affixed to the surface of layer 45 in order to enable delivery system 20 with heating pad 22 to be easily securely placed and affixed to the desired location on the skin surface of the user. As discussed above, by having cavity 46 constructed for receiving heating pad 22 substantially in its entirety, the surface of layer 45 and pad 22 is generally coextensive, thereby providing further assurance that delivery system 20 is easily securely mounted to the desired body site.

As detailed above in reference to the embodiment of FIG. 3, delivery system 20 of this embodiment also incorporates a release liner 48 which is placed in overlying protective engagement of adhesive coating 47. In this way, the adhesive material is protected until use of delivery system 20 is desired. Then, release liner 48 is removed, exposing adhesive surface 47 and enabling delivery system 20 to be securely affixed to any desired location.

In the preferred construction of this embodiment, heating pad 22 is securely affixed to layer 45 of carrier 21 by fastening means 49. Although any desired fastening means can be employed without departing from the scope of this invention, in this embodiment, wherein a single use delivery system is established, the use of a glue or cement-type fastener is preferred, with heating pad 22 securely affixed thereto during the manufacturing process.

In FIG. 4, delivery system 20 is depicted securely retained within a housing or container 50, which is shown as a generally conventional, sealable container formed from plastic sheet or film material. Generally, container 50 is formed from material which can be easily sealed during its manufacture and, preferably, be resealed by the consumer, if desired.

By employing a resealable system, heating pad 22 can be partially used and then saved by sealing pad 22 within container 50 so as to prevent contact between heating pad 22 and the atmospheric oxygen. In this way, the chemical reaction employed for achieving the desired heat is stopped as long as heating pad 22 is sealed within container 50. Whenever reuse of the heating pad is desired, delivery system 20 is removed from container 50, thereby allowing heating pad 22 to be re-exposed to the oxygen and the exothermic reaction occurs again.

By employing a resealable container 50, delivery system 20 or a removable heating pad by itself can be stored in container 50 if short term exposure is desired. In this way, the heating pad is preserved for reuse at a later time.

In FIG. 5, a final embodiment for a single use delivery system in accordance with the present invention is depicted. In this embodiment, heating pad 22 is securely affixed to a carrier 21 which is formed from any suitable material as detailed above.

In this embodiment, carrier 21 is formed from a single sheet of material, as discussed above. However, in this embodiment, excess material is removed from carrier 21, leaving an enlarged heating pad support zone 56 which provides the desired controlled oxygen flow and insulation to heating pad 22. The remainder of carrier 21 comprises two separate and independent elongated arms or strips 57 and 58 extending from opposed sides of the heating pad support zone 56. In this way, a more convenient, easily installed construction is attained, wherein elongated arms 57 and 58 are more easily wrapped around most portions of the user's body to securely retain heating pad 22 and heating pad support zone 56 of carrier 21 in the precisely desired location.

As with the embodiments detailed above in reference to FIGS. 1 and 2, this embodiment of delivery system 20 would incorporate fastening means associated therewith to enable delivery system 20 to be securely mounted to the user quickly and easily. As with the previous embodiments, a hook/look fastener construction is preferably employed with hook/loop fastener portion 59 mounted to the terminating end of arm 57, ready for cooperative locking interengagement with the opposed surface of carrier 21 where the cooperating portion of the hook/loop fastener system is securely affixed. In this way, a conveniently employed delivery system is realized which is capable of being quickly and easily mounted to the skin surface of a user in any desired location, for securely maintaining heating pad 22 in overlying therapeutic contact with the body area to be treated.

As is apparent from the foregoing detailed disclosure, the delivery system of the present invention can be manufactured in a plurality of alternate constructions for both reuse or single applications. Although a plurality of alternate embodiments has been detailed herein, these alternate embodiments have been presented for exemplary purposes in order to teach the overall concept of the delivery system of this invention, and are not intended to limit the scope of this invention.

It will thus be seen that the objects set forth above, among those made apparent from the preceding description, are efficiently attained and, since certain changes may be made in the above articles without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Having described our invention, what we claim is new and desire to secure by Letters Patent is:

1. A universally employable delivery system for providing heat therapy to any desired location on the body of a user, said system comprising:

A. a carrier
   a. constructed for being easily, securely mounted in any desired position or location on an individual, and
   b. having a cutout zone dimensioned for receiving a heat generating pad in peripheral surrounding interengagement therewith;
 B. a heat generating pad incorporating heat producing means contained therein and constructed for delivering the desired level of heat upon activation;
 C. holding means cooperatively associated with the carrier and the heat generating pad for securely maintaining the heat generating pad in secure, mounted, cooperative engagement with the cutout zone of the carrier; and
 D. mounting means cooperatively associated with the carrier for enabling the carrier to be securely mounted in any desired position on the body of the user for delivering the desired heat therapy to any particular site;

whereby a universally employable heat therapy delivery system is attained which is capable of being placed in any desired location on the body of a user for providing the desired level of heat directly to the desired location.

2. The universally employable heat therapy delivery system defined from claim 1, wherein said carrier is further defined as being formed from at least one substantially continuous layer of soft, flexible, porous material constructed for providing a desired level of heat insulation and oxygen permeability.

3. The universally employable heat therapy delivery system defined in claim 2, wherein said carrier is further defined as being formed from a foamed thermoplastic material selected from the group consisting of polyurethane, polystyrene, polyolefin, and polypropylene.

4. The universally employable heat therapy delivery system defined in claim 3, wherein said carrier is further defined comprising an overall thickness ranging between about $1/16''$ and $1/2''$ and pores having a size ranging between about 0.05 and 3.0 mm.

5. The universally employable heat therapy delivery system defined in claim 1, wherein said holding means is further defined as being constructed for removably securing a first heat generating pad in a precisely desired location on the carrier, enabling said heat generating pad to be removed from the carrier when the heat generating means has been expended and enabling a second heat generating pad to be securely affixed to the carrier in the precisely desired location after said first heat generating pad has been removed therefrom.

6. The universally employable heat therapy delivery system defined in claim 5, wherein the holding means comprises two cooperating, interlocking hook and loop fastening members, with a first hook and loop fastening member being securely affixed to the carrier and a second hook and loop fastening member being securely affixed to the heat generating pad, thereby enabling the heat generating pad to be removably affixable to the carrier.

7. The universally employable heat therapy delivery system defined in claim 6, wherein said holding means are further defined as comprising a plurality of second hook and loop fastening members, each of which are separately affixable to different heat generating pads, thereby enabling the plurality of heating pads to be separately mountable to the carrier for interengaged association therewith and removability and replacement when said heat generating pad is expended.

8. The universally employable heat therapy delivery system defined in claim 1, wherein said mounting means are defined as comprising at least two cooperating, interlocking members affixed to opposed surfaces of the carrier and positioned for mating, cooperating, interengagement with each other for securely maintaining the carrier in any desired position or location on an individual.

9. The universally employable heat therapy delivery system defined in claim 8, wherein said pair of cooperating, interlocking members are further defined as comprising hook and loop fastening means with the first of said pair of interlocking members being mounted on a first surface of the carrier in spaced, cooperating relationship with the heat generating pad mounted thereto, and a second interlocking hook and loop fastening member being is securely affixed to substantially the entire opposed surface of the carrier, whereby cooperating, locked mounted interengagement of said first and second interlocking members is quickly and easily attained at virtually any desired location or position.

10. The universally employable heat therapy delivery system defined in claim 1, wherein said mounting means is further defined as comprising an adhesive layer affixed to one surface of the carrier in association with the heat generating pad for enabling the mounting means to securely affix the carrier and heat generating pad to any desired position or location on the skin of an individual.

11. The universally employable heat therapy delivery system defined in claim 1, wherein said heat generating pad is further defined as being activated by exposure to oxygen and said delivery system is further defined as being packaged in an oxygen free, peripherally surrounding resealable container, thereby enabling a single heat generating pad to be reusably employed for short time periods by storing the delivery system in the resealable container when not in use.

12. A universally employable delivery system for providing heat therapy to any desired location on the body of a user, said system comprising:
   A. a carrier
      a. formed from at least one layer of soft, flexible, porous material selected to provide a desired level of heat insulation and oxygen permeability,
      b. constructed for being easily, securely mounted in any desired position or location on an individual, and
      c. comprising a cutout zone dimensioned for receiving a heat generating pad in peripheral surrounding interengagement therewith;
   B. a heat generating pad incorporating heat producing means contained therein and constructed for delivering the desired level of heat upon activation;
   C. holding means
      a. affixed to a first surface of the carrier layer in a substantially central location at a base of the cutout zone, and
      b. constructed for cooperative holding engagement with the heat generating pad for securely maintaining the heat generating pad in secure, mounted, engagement on the first surface of the carrier layer; and
   D. mounting means cooperatively associated with at least the first surface of the carrier layer in cooperating association with the heat generating pad, for enabling the carrier to be securely mounted in any desired position on the body of the user for securely retaining the heat generating pad in any desired location for delivering the desired heat therapy to the desired site;
whereby a universally employable heat therapy delivery system is attained which is capable of being placed in any desired location on the body of a user for providing the desired level of heat directly to the desired location.

13. The universally employable heat therapy delivery system defined in claim 12, wherein said carrier is further defined as being constructed from two layers of soft, flexible, porous material which are mounted in secure, affixed, interengagement with each other, with one of said layers incorporating a portal zone formed therein dimensioned for peripherally surrounding and interengaging with said heat generating pad in cooperating, nested relationship therewith, thereby providing an easily constructed heat therapy delivery system with the heating pad being maintained in nested interengagement with the carrier.

14. The universally employable heat therapy delivery system defined in claim 12, wherein said holding means is further defined as comprising one selected from the group consisting of adhesives and hook and loop fasteners.

15. The universally employable heat therapy delivery system defined in claim 12, wherein said mounting means is further defined as comprising
   a. at least two cooperating, interlocking members,
   b. each of said cooperating members being affixed to said first surface and an opposed surface of the carrier, and
   c. one of said cooperating members being positioned on a surface of the carrier in spaced relationship to the heat generating pad enabling the heat generating pad to be placed in any desired position on the body of the user for delivering the desired heat therapy to that particular site and retained in that position by wrapping the carrier about a portion of the user's body with the first of said pair of cooperating interlocking members being brought into locked interengagement with the second of said cooperating interlocking members.

16. The universally employable heat therapy delivery system defined in claim 15, wherein said pair of cooperating interlocking members is further defined as comprising a pair of hook and loop fasteners with the hook portion thereof being mounted to the first surface of the carrier in spaced relationship to the heat generating pad and the loop member thereof being mounted to the opposed surface of the carrier substantially covering the entire surface thereof, thereby enabling the mounting means to be placed in locked interengagement quickly and easily, in any desired position along the length thereof.

17. The universally employable heat therapy delivery system defined in claim 12, wherein said mounting means are further defined as comprising an adhesive layer applied to one surface of the carrier in peripheral surrounding relationship with the heat generating pad, thereby enabling the heat generating pad to be quickly and easily affixed to any desired position on the body of the user by applying the adhesive layer directly to the skin of the user.

18. The universally employable heat therapy delivery system defined in claim 17, wherein said adhesive layer further comprises a protective sheet removably affixed to the adhesive layer for protecting the adhesive layer from unwanted contacting interengagement with a surface prior to actual use thereof.

* * * * *